US00PP23517P3

(12) United States Plant Patent
Ferguson et al.

(10) Patent No.: US PP23,517 P3
(45) Date of Patent: Apr. 9, 2013

(54) STRAWBERRY PLANT NAMED 'DRISSTRAWTWENTYTWO'

(50) Latin Name: *Fragaria×ananassa*
Varietal Denomination: DrisStrawTwentyTwo

(75) Inventors: Michael D. Ferguson, Moorpark, CA (US); Terrance C. Moran, Ojai, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 33 days.

(21) Appl. No.: 13/136,076

(22) Filed: Jul. 22, 2011

(65) Prior Publication Data

US 2013/0025008 P1 Jan. 24, 2013

(51) Int. Cl.
*A01H 5/00* (2006.01)

(52) U.S. Cl. ..... Plt./209; Plt./208

(58) Field of Classification Search ..... Plt./208, Plt./209

See application file for complete search history.

*Primary Examiner* — Susan McCormick Ewoldt

(74) *Attorney, Agent, or Firm* — Jondle Plant Sciences Division Swanson & Bratschun, L.L.C.

(57) ABSTRACT

A new and distinct variety of strawberry plant named 'DrisStrawTwentyTwo' characterized by having medium sized, conical to an almost cylindrical shaped berries that are dark red in color, and having a medium sweetness, is disclosed.

3 Drawing Sheets

Genus and species: *Fragaria×ananassa.*
Variety denomination: 'DrisStrawTwentyTwo'.

BACKGROUND OF THE NEW PLANT

The present invention relates to a new and distinct strawberry variety designated 'DrisStrawTwentyTwo' and botanically known as *Fragaria×ananassa*. This new strawberry variety was the result of a controlled cross conducted in Ventura County, Calif. in 2006 between the proprietary female parent 'DrisStrawThree' (U.S. Plant Pat. No. 19,673) and the proprietary male parent '50L206' (unpatented). A single plant was selected for asexual propagation via tissue culture and vegetative cuttings in Shasta County, Calif. in 2007.

'DrisStrawTwentyTwo' underwent further testing in Ventura County for four years (2007-2011). The present invention has been found to retain its distinctive characteristics through several asexual propagations via stolons.

Plant Breeder's Rights for this variety have not been applied for. 'DrisStrawTwentyTwo' has not been made publicly available or sold more than one year prior to the filing date of this application.

DESCRIPTION OF THE PHOTOGRAPHS

The accompanying color photographs show typical specimens of the new variety at various stages of development. The colors shown are as true as can be reasonably obtained by conventional photographic procedures. The photographs were taken on four-month-old plants.

DESCRIPTION OF THE NEW VARIETY

Figure 1:
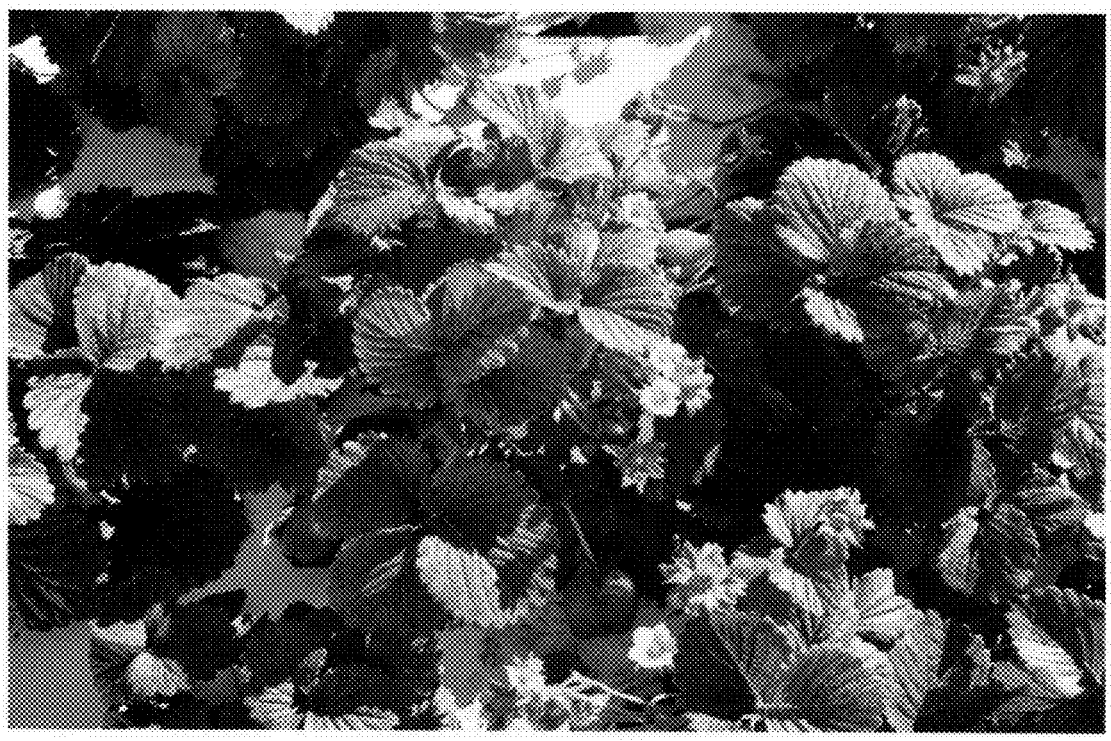
FIG. 1 shows overall plant habit including fruit at various stages of development.
Figure 2:
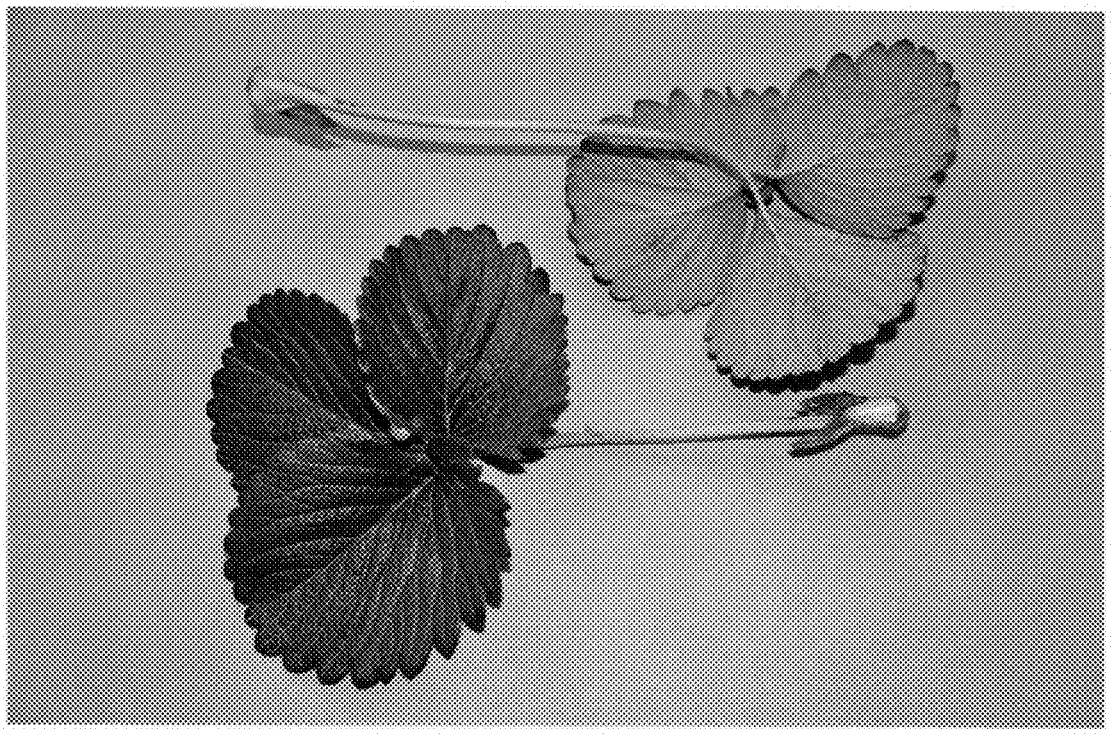
FIG. 2 shows leaves of the plant with three leaflets.
Figure 3:
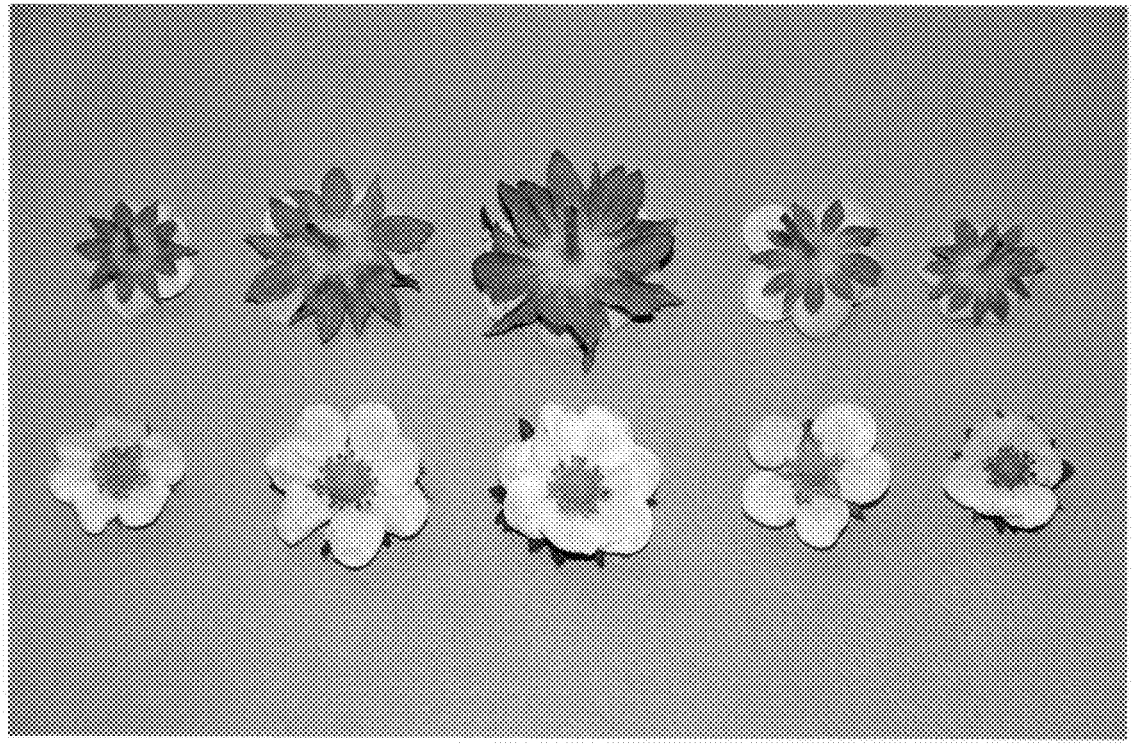
FIG. 3 shows both upper and lower surfaces of the flowers.
Figure 4:
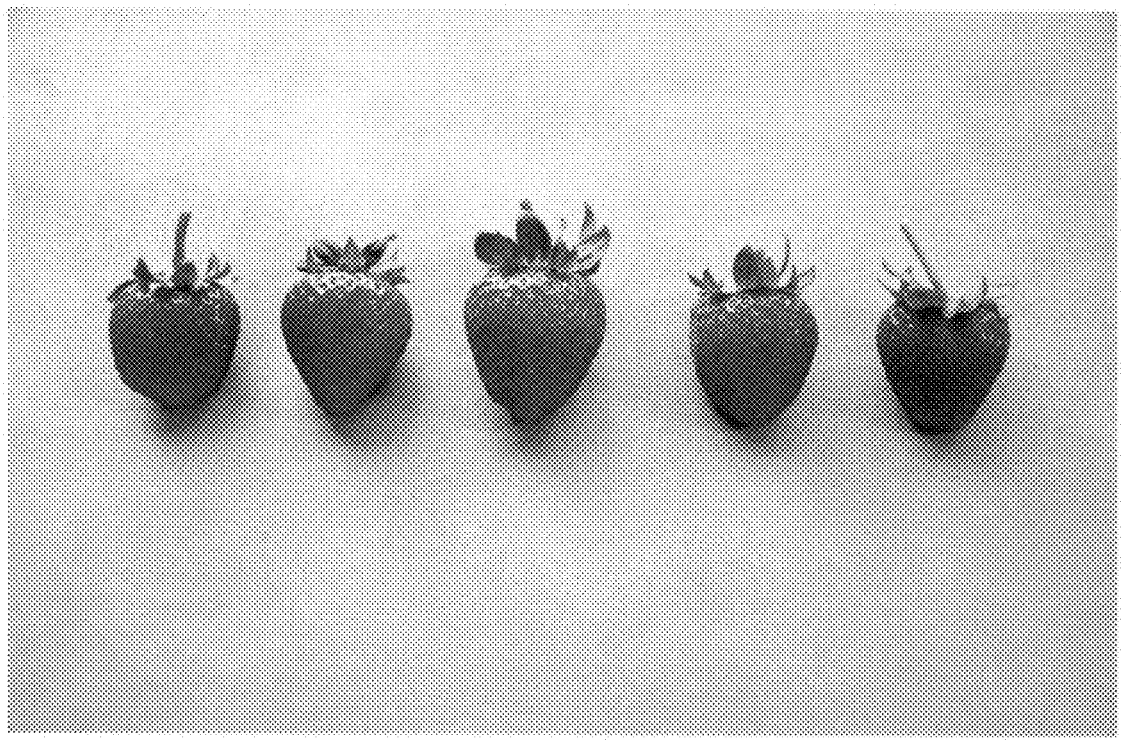
FIG. 4 shows the whole fruit.
Figure 5:
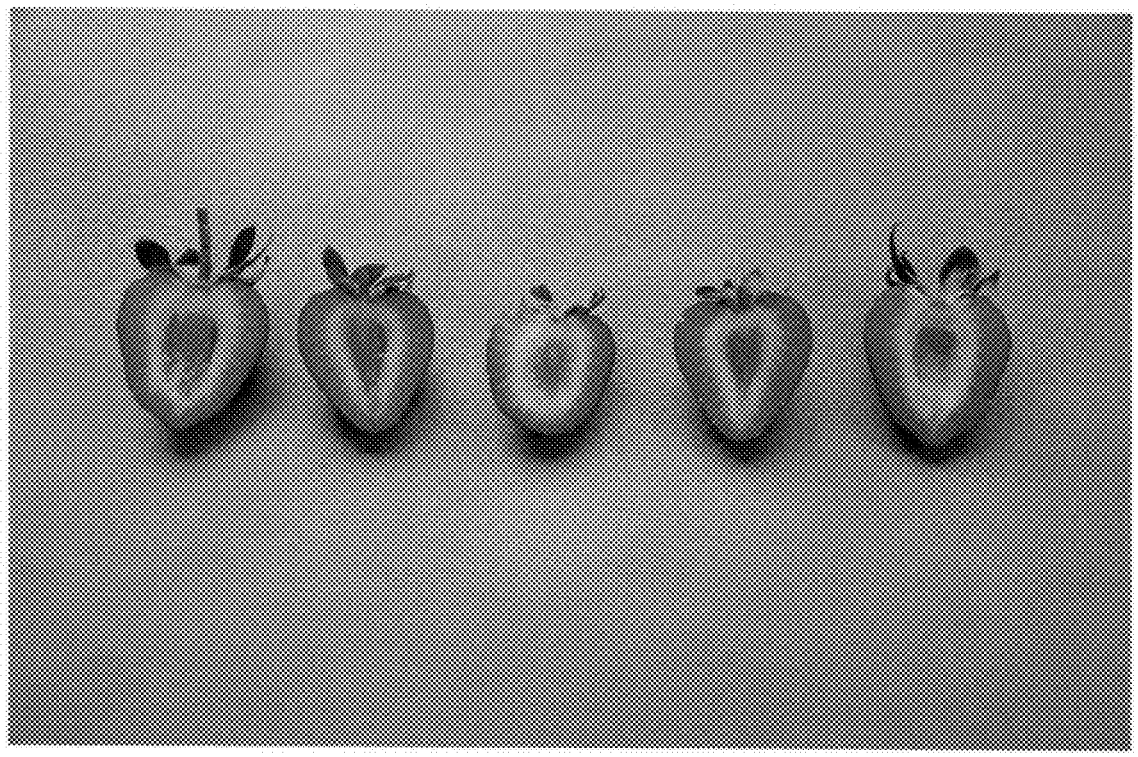
FIG. 5 shows the fruit in longitudinal cross-section.

The following detailed descriptions set forth the distinctive characteristics of 'DrisStrawTwentyTwo'. The data which define these characteristics is based on observations taken in Ventura County, Calif. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentyTwo' has not been observed under all possible environmental conditions. The botanical description of 'DrisStrawTwentyTwo' was taken from four-month-old plants. Color terminology follows The Royal Horticultural Society Colour Chart, London (R.H.S.) (2001).

DETAILED BOTANICAL DESCRIPTION OF THE PLANT

Classification:

*Species.*—*Fragaria×ananassa.*
*Common name.*—Strawberry.
*Denomination.*—'DrisStrawTwentyTwo'.

Parentage:

*Female parent.*—The proprietary variety 'DrisStrawThree' (U.S. Plant Pat. No. 19,673).
*Male parent.*—The proprietary variety '50L206' (unpatented).

Plant:

*Height.*—23.0 cm.
*Diameter.*—45.4 cm.
*Number of crowns/plant.*—3.
*Habit.*—Globose — semi-upright.
*Density of individual plant.*—Dense.
*Vigor.*—Medium.

Leaves:
*Leaf length.*—20.0 cm.
*Leaf width.*—20.0 cm.
*Terminal leaflet length.*—8.1 cm.
*Terminal leaflet width.*—8.7 cm.
*Terminal leaflet length/width ratio.*—0.9 (as long as broad).
*Number of teeth/terminal leaflet.*—23.
*Shape of teeth.*—Rounded-crenate.
*Color.*—Upper surface: RHS 137A (Dark green). Lower surface: RHS 148B (Medium yellow-green).
*Leaf shape in cross section.*—Slightly concave.
*Leaf blistering.*—Weak.
*Leaf glossiness.*—Medium.
*Number of leaflets.*—3 only.
*Terminal leaflet margin profile.*—Revolute (margins rolled backwards).
*Terminal leaflet shape.*—Orbicular.
*Terminal leaflet base shape.*—Obtuse.
*Terminal leaflet apex descriptor.*—Rounded.
*Terminal leaflet size.*—Large.
*Terminal leaflet variegation.*—Absent.
*Terminal leaflet margin.*—Serrate.

Petiole:
*Length.*—Short; 14.1 cm.
*Diameter.*—3.52 mm.
*Pubescence.*—Lightly puberulent.
*Pose of hairs.*—Outwards — horizontal.
*Color.*—RHS 145A (Medium yellow-green).

Petiolule:
*Color.*—RHS 146C (Medium yellow-green).
*Length.*—11.96 mm.
*Diameter.*—1.75 mm.
*Bract frequency.*—0.

Stipule:
*Length.*—3.5 cm.
*Width.*—10.99 mm.
*Pubescence.*—Medium.
*Stipule anthocyanin coloration.*—Absent or very weak.

Stolon:
*Number.*—Few.
*Average number of daughter plants per plant.*—45.
*Stolon anthocyanin coloration.*—Very strong.
*Stolon anthocyanin color.*—RHS 60A (Dark red-purple).
*Thickness.*—Thick.
*Pubescence.*—Dense.

Inflorescence:
*Position relative to foliage.*—Beneath.
*Number of flowers.*—40.
*Time of flowering* (*50% of plants at first flower*).—May 1 to January 1.
*Flower size.*—Medium.
*Diameter.*—31.74 mm.
*Petals.*—Shape: Orbicular. Apex: Rounded. Base: Concave-convex. Margin: Entire. Spacing: Overlapping. Length: 15.29 mm. Width: 14.69 mm. Length/width ratio: 1.0; as long as broad. Typical petal number per flower: 6. Observed petal number per flower: 5 to 7. Color (upper surface): RHS 155B (White).
*Calyx.*—Diameter: 32.42 mm. Diameter relative to corolla: Same size. Inner calyx diameter relative to outer: Same size.
*Sepal.*—Shape: Elliptical. Apex: Convex. Margin: Entire. Length: 11.32 mm. Width: 5.73 mm. Typical sepal number per flower: 12. Observed sepal number per flower: 10 to 14. Receptacle color: RHS 2B (Medium yellow). Anther color: RHS 13B (Medium yellow). Stamen: Present.
*Pedicel.*—Attitude of hairs: Slightly upwards.

Fruiting truss:
*Length.*—Medium; 18.5 cm.
*Diameter at base of truss.*—3.89 mm.
*Number of berries per fruiting truss.*—5.
*Attitude at first picking.*—Prostrate.
*Color at base of truss.*—RHS 145A (Medium yellow-green).

Fruit:
*Length.*—44.45 mm.
*Width.*—40.66 mm.
*Length/width ratio.*—1.1 (as long as broad).
*Fruit hollow length.*—19.48 mm.
*Fruit hollow width.*—10.96 mm.
*Fruit hollow length/width ration.*—1.8.
*Fruit hollow center* (*cavity*).—Large.
*Weight* (*per individual berry*).—30.6 g.
*Relative fruit size.*—Medium.
*Predominant fruit shape.*—Conical and almost cylindrical.
*Difference in shape between primary and secondary fruits.*—None or very slight.
*Unevenness of fruit surface.*—Slightly uneven.
*Fruit skin color.*—RHS 46A (Dark red).
*Evenness of fruit color.*—Even or very slightly uneven.
*Fruit glossiness.*—Medium.
*Insertion of achenes.*—Below surface.
*Achene coloration* (*sunward side of berry*).—RHS 183A (Dark greyed-purple).
*Achene coloration* (*shaded side of berry*).—RHS 153C (Medium yellow-green).
*Achenes per berry.*—384.
*Achene weight* (*weight of achenes in grams divided by total # seed*).—0.000567526 g.
*Band without achenes.*—Narrow.
*Insertion of calyx.*—Level.
*Pose of calyx segments.*—Reflexed — upwards.
*Size of calyx in relation to fruit.*—Slightly larger.
*Adherence of calyx.*—Very strong.
*Firmness of flesh.*—Firm.
*Color of flesh* (*excluding core*).—RHS 43A (Medium red) and RHS 155D (White).
*Color of core.*—RHS 46A (Dark red) and RHS N155B (White).
*Evenness of flesh color.*—Even.
*Distribution of flesh color.*—Marginal and central.
*Sweetness.*—Medium.
*Acidity.*—Medium.
*Texture when tasted.*—Coarse.
*Type of bearing.*—Fully everbearing — fully remontant.
*Grams of fruit/plant.*—285.1.
*Harvest interval.*—Late September to mid-December.
*Harvest maturity.*—Mid-season.

COMPARISON WITH PARENTAL AND COMMERCIAL VARIETIES

When 'DrisStrawTwentyTwo' is compared to the proprietary female parent 'DrisStrawThree' (U.S. Plant Pat. No. 19,673), 'DrisStrawTwentyTwo' has smaller fruit, firmer fruit, and less sweet than 'DrisStrawThree'. Additionally, 'DrisStrawTwentyTwo' is more vigorous and has lower yields.

When 'DrisStrawTwentyTwo' is compared to the proprietary male parent '50L206', 'DrisStrawTwentyTwo' is less vigorous, has higher yields, better flavor, and more conic shaped fruit.

When 'DrisStrawTwentyTwo' is compared to the commercial variety 'DrisStrawSeventeen' (U.S. Plant Pat. No. 22,218), 'DrisStrawTwentyTwo' has medium-sized fruit, with a medium red and white fruit flesh color, a conical and almost cylindrical fruit shape, slightly even fruit surface and medium vigor, while 'DrisStrawSeventeen' has very large sized fruit, with a medium orange red and white fruit flesh color, a wedged shape, strong unevenness of fruit surface and very strong vigor.

We claim:

1. A new and distinct variety of strawberry plant as described and shown herein.

* * * * *